United States Patent [19]

Paris et al.

[11] 4,137,317

[45] Jan. 30, 1979

[54] GLYCERIDES WITH ANTIBACTERIAL PROPERTIES

[75] Inventors: Gerald Y. Paris, Duvernay; Denis G. Cimon, Montreal North; David L. Garmaise, Montreal, all of Canada

[73] Assignee: Abbott Laboratories, North Chicago, Ill.

[21] Appl. No.: 851,003

[22] Filed: Nov. 14, 1977

Related U.S. Application Data

[63] Continuation-in-part of Ser. No. 638,246, Dec. 8, 1975, abandoned, and Ser. No. 754,299, Dec. 27, 1976, abandoned.

[51] Int. Cl.$^2$ .................. A61K 31/455; C07D 471/04

[52] U.S. Cl. .................. 424/256; 260/239.1; 544/28; 544/234; 544/279; 424/258; 424/271; 546/123; 546/90

[58] Field of Search .................. 260/295.5 B; 424/256

[56] References Cited

PUBLICATIONS

Chauvette et al., J. Med. Chem., vol. 9, No. 5, pp. 741-745, (1966).

*Primary Examiner*—Alan L. Rotman
*Attorney, Agent, or Firm*—Paul D. Burgauer; Robert L. Niblack

[57] ABSTRACT

Triglycerides carrying an anti-bacterial drug moiety in the 2-position and a hydrocarbon acyl moiety in the 1- and 3-positions exhibit excellent anti-bacterial properties without causing the side effects often associated with oral antibiotics when used by themselves.

8 Claims, No Drawings

GLYCERIDES WITH ANTIBACTERIAL PROPERTIES

CROSS REFERENCE TO RELATED APPLICATIONS

This application is a continuation-in-part of our earlier application, Ser. No. 754,299, filed on Dec. 27, 1976, and Ser. No. 638,246 filed on Dec. 8, 1975, both now abandoned.

DETAILED DESCRIPTION OF THE INVENTION

Anti-bacterials are used widely in the treatment of various bacterial infections. Today, many anti-bacterials are used for gastro-intestinal or urinary tract infections; they are given orally, since this is obviously the simplest form of administration. However, some of the anti-bacterials used create gastric irritations, particularly when these drugs are to be taken over an extended period of time. These irritations manifest themselves in pains, cramps, stomach discomforts etc.; they can be shown experimentally in animals which develop lesions, ulcers, gastric bleeding etc.

It is therefore an object of the present invention to provide an anti-bacterial composition that shows improved tolerance by the gastric tract of warm-blooded animals; it is a further object of this invention to provide an anti-bacterial composition for oral administration which causes minimal or no stomach irritation; it is a particular object of this invention to provide new and better tolerated anti-bacterials that are effective upon oral administration.

These and other objects are accomplished by providing a compound of the formula:

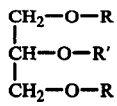

I wherein R is an acyl derivative of the formula $CH_3-X-CO-$ wherein X represents a single bond or a saturated or unsaturated divalent chain of two to eighteen carbon atoms and wherein R' is the acyl moiety of an organic, pharmaceutically acceptable acid having antibacterial properties.

The above acyl moiety having anti-bacterial properties are the active principles of many important anti-bacterial compounds in use today and represent some of the most frequently described anti-bacterials which, however, may cause various unpleasant side-effects to the patient. R' includes specifically the acyl derivatives of nalidixic acid (the 1-ethyl-1,4-dihydro-7-methyl-4-oxo-1,8-naphthyridine-3-carboxylic acid, the acyl moiety of which will hereinafter be called nalidixoyl), piromidic acid, cinoxacin, oxolinic acid, penicillins, cephalosporins and other known gram-positive or gram-negative anti-bacterials which carry a free carboxylic acid group.

Concerning substituent R, the acyl group contains a total of between two and twenty carbons and in the formula given above, X preferably represents the moiety $-(CH_2)_n-$ wherein n is 0 or an even integer; more specifically, acetyl, butyryl, hexanoyl, octanoyl, dodecanoyl, palmitoyl and the like. X can also be an unsaturated hydrocarbon chain, containing one or more double bonds. R can thus be the acyl moiety of acrylic, crotonic, linoleic, undecanic and oleic acid and the like.

In a general embodiment of the present invention, glycerol is first oxidized by known methods to form dihydroxyacetone. This compound is diesterified with the desired acid of formula $CH_3XCOOH$ to form the corresponding 1,3-dialkanoylglycerol (the term "alkanoyl" hereinafter is intended to represent $CH_3XCO-$ with X having the above meaning), which, in turn, is then esterified with the acid chloride of a known anti-bacterial having a free carboxylic acid group. The preparation of such an acid chloride of a known anti-bacterial can ordinarily be carried out in known fashion by the use of phosphorous pentachloride, thionyl chloride, phosphorous oxy-chloride or other inorganic agents ordinarily used for such a conversion. These acid chlorides are usually quite stable and quite reactive so that the condensation or esterification with the 1,3-dialkanoyl-glycerol ordinarily produces a yield of 60 to 100% of theory. Obviously, the diesterified dihydroxyacetone must first be reduced to the corresponding dialkanoyl-glycerol (formula I: R = alkanoyl; R' = H).

In a more specific embodiment, dihydroxyacetone suspended in chloroform is cooled and after adding a minor proportion of pyridine, at least 2 molar equivalents of an alkanoyl chloride is added dropwise over a period of time. After stirring for several hours in an ice bath, the formed precipitate is removed and the 1,3-dialkanoyl dihydroxyacetone is worked up in known fashion. It is then taken up in a suitable solvent or solvent mixture and reduced, preferably using neutral sodium borohydride which produces the desired 1,3-dialkanoylglycerol which is isolated from the mixture in known fashion. This compound is then reacted, for instance, with about one equimolar amount of the acid chloride of nalidixic acid in the presence of a hydrochloric acid acceptor and a suitable organic solvent. Upon isolation and recrystallization, the formed triester of formula I is obtained in good purity.

Compounds made in this fashion can easily be compounded into dosage unit form for medicinal use. For instance, pharmaceutical tablets can be prepared by mixing this material with the usual type of adjuvants, flavoring agents, fillers, buffers and/or coloring agents which together with a lubricant can be compressed into the usual tablets. Also, a mixture of the above active compound with fillers and/or buffers or solid diluents can be processed into wafers, pills, or just simply filled into gelatin capsules in dosages of suitable amounts. Preferably, a dosage unit contains between 250 and 1250 mg. of the active ingredient, and tablets of this type are preferably prepared in bisected form.

Oral dosage forms of the type indicated above do not require any coating for the purpose of taste masking or protection against the acid environment of the stomach. The active ingredient is of very low acid and water solubility so that the taste requires no or little masking and stomach irritation is almost totally absent. Also, when the active ingredient reaches the intestinal tract, absorption takes place without irritating the gut. The active ingredient is lipid soluble and as such penetrates the cell membranes and will be found in the blood stream at sufficiently high doses to provide anti-bacterial effects without irritating side effects for the intestinal or gastric tract.

In order to illustrate the method for preparing and using the new triglycerides, reference is made to the following examples which, however, are not meant to limit the invention in any way.

EXAMPLE 1

To a cold solution of 1.16g nalidixic acid in 75ml of chloroform is added 0.64g of oxalyl chloride. The mixture is stirred for one hour at 0° and then allowed to warm up to room temperature where it is stirred for an additional 30 minutes. A solution of 2.29g of 1,3-dilaurylglycerol and 0.95g of dry pyridine in 25ml of chloroform is added. A red color develops immediately. The reaction mixture is stirred for four days at room temperature and evaporated to dryness. After adding 200ml of ether to the residue, the insoluble portion is removed by filtration and the ether extract is washed with two 25ml portions of water, two 25ml portions of 1% aqueous hydrochloric acid, once with 25ml of water, twice with 25ml of 1% aqueous sodium bicarbonate, twice with 25ml of water, once with 25ml of brine and finally dried over magnesium sulfate. Removal of solvent yields an oil which crystallizes on standing. Recrystallization from methanol produces a white solid melting at 47°–50° in a yield of 1.9g of 2-nalidixoyl-1,3-didodecanoylglycerol.

In a standard test used to determine the necessary dose at which one half of test animals infected with E.coli are cured from a lethal dose of the microorganism ($CD_{50}$), it is found that the oral $CD_{50}$ is three times the dose necessary for nalidixic acid per se on a molecular basis. However, the new compound shows no toxicity at levels of 2g per kilo upon oral administration to mice and causes no gastric irritation at that level.

When the above nalidixic acid is replaced with 1.44g of piromidic acid, 2-[8-ethyl-5,8-dihydro-5-oxo-2-(1-pyrrolidinyl)pyrido[2,3-d]pyrimidine-6-carbonyloxy]-1,3,-didodecanoylglycerol is obtained, showing similar $CD_{50}$ and toxicity properties as the reported nalidixoyl glyceride.

EXAMPLE 2

2-Nalidixoyl chloride is prepared as described in Example 1 by reacting 1.27g of oxalyl chloride with 2.32g of nalidixic acid in 150ml of dry chloroform. A solution of 1.76g of 1,3-diacetylglycerol and 1.74g of dry pyridine in 25ml of chloroform is then added. The red color develops as in Example 1 and the reaction mixture is stirred for four days at room temperature and then treated first with 50ml of brine containing 1% hydrochloric acid and then with 50ml of brine. The chloroform extracts are dried over magnesium sulfate and evaporated to dryness. The residue is triturated with 100ml of ether and the insoluble nalidixic acid is filtered (1.5g). The filtrate is washed with 50ml of brine containing 1% sodium hydroxide. A solid forms at the interface and is filtered, yielding 0.55g of 2-nalidixoyl-1,3-diacetylglycerol, melting at 146°–148° C. after one crystallization from chloroform/petroleum ether.

In a mouse protection test carried out in standard fashion, oral administration of this compound shows a $CD_{50}$ of about 100mg per kg upon a single-day, b.i.d. oral administration.

When the above nalidixic acid is replaced with 1.42g of oxolinic acid or 1.43g of cinoxacin, one obtains 1,3-diacetyl-glycerol carrying as R' the 5-ethyl-5,8-dihydro-8-oxo-1,3-dioxolo[4,5-g]quinoline-7-carbonyl group or the 1-ethyl-1,4-dihydro-4-oxo-1,3-dioxolo[4,5-g]cinnoline-3-carbonyl group respectively. Both of these new compounds manifest no lesions in the G.I. tract even when orally administered at doses far exceeding the $CD_{50}$ levels.

EXAMPLE 3

Pyridine (0.4ml, 0.0050 mole) is added slowly to a stirred suspension of 1.0g of cephalothin (3-hydroxymethyl-8-oxo-7-[2-(2-thienyl)-acetamido]-5-thia-1-azabicyclo[4,2,0]-oct-2-ene-2-carboxylic acid acetate) and 5.0g of 1,3-didecanoylglycerol in 25ml of dry dichloroethane with cooling to 0°–5° C. After adding 0.56g of dicyclohexylcarbodiimide, the reaction mixture is stirred at ambient temperature for twenty hours. The insoluble dicyclohexylurea is removed by filtration and the filtrate is washed, in turn, with 50ml of 5% HCl, 50ml of water, 50ml of 5% $NaHCO_3$, 2 × 50ml of water, and dried over magnesium sulfate. The solution is then concentrated to a volume of about 10ml and hexane is added until a precipitate starts to form. The solid is filtered off. The new filtrate is decolorized with charcoal and by addition of more hexane a white solid is obtained representing the desired 2-cephalothin-1,3-didecanoylglycerol. Yield 570mg, m.p. 98.5°–100° C.

In view of the extremely low toxicity of the above triglyceride of structure I and the extremely low incidence of lesions and gastric irritations, the new compounds are of great value in the treatment of bacterial infections. They can be administered over extended periods of time without danger of gastric or intestinal bleedings, ulcers or the milder forms of irritations and upsets as is often the case with the free acids currently used. The new compounds have extremely favorable therapeutic indices as in most instances, no toxicity could be established even with massive doses.

It will be obvious to those skilled in the art that the dosage of the new triglycerides to be administered to a large extent depends on the anti-bacterial moiety in the triglyceride. Thus, for instance, where R' in the new triglyceride is the nalidixoyl moiety, a rather large dose is needed, but such a dose is tolerated without discomfort. When R' is the acyl moiety of penicillin, the total daily dose or single effective dose to be administered is much smaller. The dose also depends somewhat on the type of esters used for the 1- or 3-positions in the triglyceride. When R is a small moiety, i.e., X contains 0, 2, 4 or 6 carbon atoms, the proportion of R' in the triglyceride is considerably higher than when the compound is used wherein X contains 12 to 18 carbons. Thus, the desired dosage depends on the therapeutic activity of R' and is indirectly dependent on the length of the aliphatic chain in the 1- and 3-positions.

In order to prepare capsules for oral administration, the following procedure is employed: 25g of the compound of Example 1 is preblended with 112g of lactose and 12.5g of talcum powder. The preblend is passed through a suitable screen and the screened powder is then blended and filled into gelatin capsules No. 3 to produce a filled weight of 250mg per capsule.

The following formulation is a typical tablet formula which may be used to incorporate the compounds of the present invention into tablet form: 52g of corn starch, 500g of the above triglyceride, 228g of calcium phosphate dibasic dihydrate, 4g of magnesium stearate and 16g of talcum powder with water q.s. to 800g. Part of the above corn starch is milled together with the active drug and the calcium phosphate; this blend is milled and passed through a 40-mesh screen. The remaining portion of the corn starch is granulated with water, heated and mixed with the above blend in a hot air oven at 50°

C. and sifted through a 16-mesh screen. The talcum powder and magnesium stearate are then added, the mixture is blended and subsequently passed through a 30-mesh screen and blended for at least 15 minutes. In order to prepare tablets, this mixture is compressed using a 9/32" standard convex punch producing a tablet of hardness 7 to 9 with each tablet weighing 800mg and containing 500mg of the active drug.

Of course, other pharmaceutically acceptable compositions can easily be prepared, e.g., suspensions, syrups, pills, wafers, and the like, preferably containing a predetermined amount of the active ingredient per given volume of such a dosage form. In case of liquid preparations for oral ingestion, a suitable nontoxic vehicle is used containing the necessary flavoring and sweetening agents to make up a liquid that is pleasant in taste and mouth feel.

Aside from the above demonstrated nalidixic acid, penicillin and cephalosporin derivatives, it will be obvious to those skilled in the art that 1,3-diacyl-2-glycerides of other basic or generic groups of antibacterial acids can be made as well, for instance from the acyl moieties of benzylpenicillin, phenoxymethyl penicillin, phenethicillin, cloxacillin, dicloxacillin, methicillin, oxacillin, ampicillin, carbenicillin, epicillin, hetacillin, pivampicillin, and the like can be substituted therefor. Their acyl moieties will take the place of R' in formula I and are intended to be included in the scope of this invention. It will also be recognized that some of these final structures will produce gram-negative, gram-positive or a combination gram-positive and -negative antibacterial response, depending entirely on the activity of the starting material R'OH used in making the compound of structure I.

We claim:

1. A compound of the formula

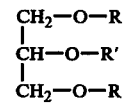

wherein R is an acyl derivative of the formula $CH_3-X-CO-$ wherein X represents a single bond or a saturated or unsaturated divalent carbon chain of 2–18 carbon atoms and wherein R' is the acyl moiety of a pharmaceutically acceptable chemically prepared carboxylic acid having anti-bacterial properties.

2. The compound of claim 1 wherein X is $-(CH_2)_{10}-$ and R' is nalidixoyl.

3. The compound of claim 1 wherein X is a single bond and R' is nalidixoyl.

4. An antibacterial composition consisting essentially of a compound of the formula

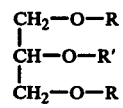

wherein R is an acyl derivative of the formula $CH_3-X-CO$ and wherein X is a divalent aliphatic chain of 0 to 18 carbon atoms and wherein R' is the acyl moiety of a pharmaceutically acceptable chemically prepared carboxylic acid having anti-bacterial properties, together with an inert pharmaceutically acceptable carrier, in dosage unit form.

5. The composition of claim 4 in the form of a tablet for oral ingestion.

6. The composition of claim 4 wherein X is $-(CH_2)_{10}-$ and R' is nalidixoyl.

7. The compound of claim 1 wherein X is a single bond or a divalent carbon chain of 2–18 carbon atoms and R' is nalidixoyl.

8. The composition of claim 4 wherein X is a single bond and R' is nalidixoyl.

* * * * *